United States Patent [19]
Johnson et al.

[11] Patent Number: 5,169,942
[45] Date of Patent: Dec. 8, 1992

[54] METHOD FOR MAKING 2-(18F)FLUORO-2-DEOXY-D-GLUCOSE

[75] Inventors: Bruce F. Johnson, Scotia; Donald H. Maylotte, Schenectady; Cheryl L. Sabourin, Albany, all of N.Y.

[73] Assignee: General Electric Company, Schenectady, N.Y.

[21] Appl. No.: 795,575

[22] Filed: Nov. 21, 1991

[51] Int. Cl.$^5$ .......................... C07H 1/00; C08B 37/00
[52] U.S. Cl. .................................. 536/122; 536/18.4; 536/18.5; 536/124
[58] Field of Search ..................... 536/122, 124, 18.4, 536/18.5

Primary Examiner—Ronald W. Griffin
Attorney, Agent, or Firm—William A. Teoli; William H. Pittman

[57] ABSTRACT

A method is provided for making 2-[$^{18}$F]fluoro-2-deoxy-D-glucose which employs a phase-transfer reagent, consisting of a tetraalkylammonium bicarbonate, a tetraalkylammonium carbonate, or a mixture of a tetraalkylammonium hydroxide and potassium bicarbonate.

6 Claims, No Drawings

METHOD FOR MAKING 2-(18F)FLUORO-2-DEOXY-D-GLUCOSE

BACKGROUND OF THE INVENTION

The present invention relates to a method for synthesizing 2-fluoro-2-deoxy-D-glucose with an [18F]fluoride ion prepared without addition of a carrier to produce a radiopharmaceutical for Positron Emission Tomography (PET). More particularly, the present invention relates to a method for making 2-[;8F]fluoro-2-deoxy-D-glucose involving the replacement of the trifluoromethanesulfonyl group (triflate) with an [18F]fluoride ion, in 1,3,4,6-tetra-O-acetyl-2-triflate-β-D-mannopyranose, where a phase-transfer catalyst is used in the form of a tetraalkylammonium bicarbonate, or a mixture of a tetraalkylammonium hydroxide and an alkali bicarbonate. Prior to the present invention, various procedures were used for making 2-[18F]fluoro-2-deoxy-D-glucose or "[18F]2FDG", which is the most widely used radiopharmaceutical ositron Emission Tomography (PET). Considerable effort has been expended in the development and refinement of such procedures. Because of its decay energy, (0.64 MEV) the [18F]fluoride ion allows the highest inherent resolution during PET measurements and has a relatively convenient half life of 109.7 min. The following equation illustrates the preferred procedure for making [18F]2FDG:

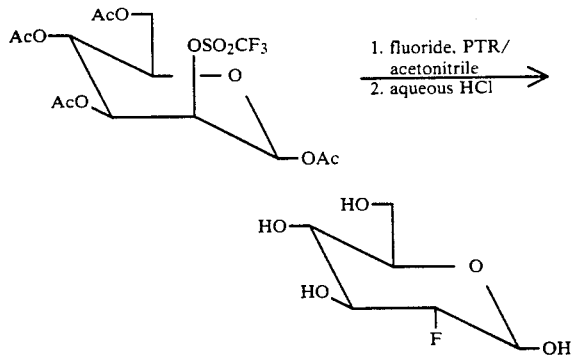

where Ac is acetate, and PTR is phase-transfer reagent.

One methOd of synthesizing [18F]2FDG by the above procedure is shown by Hamacher et al., Journal of Nuclear Medicine, 27:235-238, (1986). Hamacher et al. employ an aminopolyether [Kryptofix 222 or K222]-potassium carbonate complex as a phase-transfer catalyst for [18F]fluoride. An additional procedure for making [18F]2FDG is shown by Brodack et al., Applied Radiation and Isotope, Volume 39, No. 7, pages 699-703 (1988) involving the employment of a tetrabutylammonium hydroxide as a phase-transfer catalyst in place of the aminopolyether potassium complex of Hamacher et al. Although Brodack et al. disclose that the triflate reacts with [18F]fluoride ion using the tetrabutylammonium counter ion, a yield of 12-17% is reported which is significantly below the level considered acceptable for commercial robotic production of [18F]2FDG.

SUMMARY OF THE INVENTION

The present invention is based on a discovery that significantly improved yields of [18F]2FDG can be obtained using the above shown synthesis, by substituting for tetraalkylammonium hydroxide as the phase-transfer reagent, a mixture of substantially equal molar amounts of tetraalkylammonium hydroxide and potassium bicarbonate. In addition, further improvements in [18F]2FDG yields can be realized if tetraalkylammonium bicarbonates, such as tetraethylammonium bicarbonate or tetrabutylammonium bicarbonate are used directly as the phase-transfer reagents.

STATEMENT OF THE INVENTION

There is provided by the present invention, a method for making 2-[18F]fluoro-2-deoxy-D-glucose which comprises, (1) contacting 1,3,4,6-tetra-O-acetyl-2-0-trifluoromethanesulfonyl-2-deoxy-β-D-mannopyranose and [18F]fluoride ion in the presence of an inert organic solvent at a temperature of 40° C. to 100° C. and a phase-transfer reagent selected from the class consisting of a tetraalkylammonium bicarbonate, a tetraalkylammonium carbonate and a mixture of a tetraalkylammonium hydroxide and alkali metal bicarbonate, and (2) effecting the substantial removal of the organic solvent, and (3) heating the resulting mixture of (2) in the presence of an aqueous hydrogen halide until deprotection of the resulting acetylated 2-[18F]fluoro-2-deoxy-D-glucose is effected.

The term tetraalkylammonium bicarbonate or "TAAHCO3" will mean, hereinafter, specific compounds such as tetraethylammonium bicarbonate, tetrabutylammonium or tetrahexylammonium bicarbonate, or a mixture of substantially equal molar amounts of tetraalkylammonium hydroxide and alkali metal bicarbonate such as potassium bicarbonate. In forming the TAAHCO3 phase-transfer reagent by combining KHCO3 and tetraalkylammonium hydroxide, the KHCO3 can be added to a mixture of tetraalkylammonium hydroxide and an organic solvent, such as acetonitrile and [18F]fluoride ion in water enriched with H2 18O, resulting from the bombardment of the H2 18O with high energy protons or in sterile water added after removal of the enriched water. In instances where tetraalkylammonium bicarbonate is used directly as the phase-transfer reagent, it can be prepared by the following procedure:

CO2 is bubbled through an aqueous solution of tetraalkylammonium hydroxide (5 | 25 weight%, pH>12) until the pH has stabilized at 7-8. The flask can be evacuated to remove excess CO2, concentrated to remove water and taken up in CH3CN. The concentration of the tetraalkylammonium bicarbonate can be confirmed by treating a known volume of the solution with excess acetic acid and measuring the volume of CO2 released.

If desired tetraalkylammonium carbonate also can be used as a phase-transfer catalyst which can be formed as follows:

CO2 is bubbled through an aqueous solution of a known volume of tetraalkylammonium hydroxide (5-25 weight%, pH>12) until the pH has stabilized at 7-8. The flask is evacuated to remove CO2 and then the same volume of tetraalkylammonium hydroxide is added. The solution can be concentrated and taken up in CH3CN. The concentration of the tetra-alkylammonium carbonate can be confirmed by treating a known volume of the solution with excess acetic acid and measuring the volume of CO2 released.

In the practice of the preferred form of the invention, the $TAAHCO_3$, as an organic solvent solution, can be added along with the [$^{18}F$]fluoride ion in sterile water, to a suitable reaction vessel having a sufficient amount, such as 60 to 95 volume %, of an organic solvent based on the total volume of mixture. Inert organic solvents which can be used are for example acetonitrile, and propionitrile. The resulting mixture can then be concentrated at a pressure in the range of from 0.5 to 5 torr under an inert atmosphere such as helium, along with vigorous stirring with the flask in an oil bath set at 40° C. to 80° C. If desired, after the first concentration, a second aliquot of organic solvent can be added and the concentration repeated. The 1,3,4,6-tetra-O-acetyl-2-triflate-β-D-mannopyranose, referred to hereinafter as "triflate", can be added to the resulting mixture as an organic solvent solution. The resulting mixture can then be agitated for an additional period such as from 4 to 15 minutes under inert gas atmosphere with the flask in an oil bath set at 60° C. to 100° C. After evaporation of the organic solvent in vacuo, an aqueous hydrogen halide solution such as a solution of HCl having a 1 to 2 normality can be added to the resulting mixture. The mixture can be heated for an additional period of time such as from 10 to 25 minutes in an oil bath set at 110° C. to 130° C. under an inert gas atmosphere.

Recovery of the [$^{18}F$]2FDG can be achieved by passing the reaction mixture through quaternary amine functionalized silica or ion retardation resin to effect neutralization, a C18 reverse-phase silica or charcoal can be used to effect decolorization and neutral alumina can be used to remove unreacted fluoride. If desired, the tetraethylammonium ion can be removed by first passing the reaction mixture through sulfonic acid functionalized polystyrene resin or sulfonic acid functionalized silica; the yield of [$^{18}F$]2FDG is not affected by this last treatment. Quantification of the [$^{18}F$]2FDG can be done with TLC coupled with BioScan analysis of the TLC plate and total radioactivity measurement of the sample with a Capintec detector.

In order that those skilled in the art will be better able to practice the present invention, the following examples are given by way of illustration and not by way of limitation. All parts are by weight unless otherwise indicated.

EXAMPLE 1

Tetraethylammonium bicarbonate was prepared as follows:

40 ml of a 25% w/v solution of tetraethylammonium hydroxide (Kodak) was treated with 80 ml of water. The pH of this mixture (1 ml treated with 9 ml of water) was 12.7. The solution was treated with $CO_2$ until the pH had stabilized at 7.6. The reaction mixture was concentrated, taken up in acetonitrile (175 ml) and filtered to yield a solution of tetraethylammonium bicarbonate ready for use.

After bombardment, water enriched with $H_2^{18}O$, was recovered by distillation of the contents in a cyclotron target cell. The residue in the distillation pot (which Contained the $^{18}F$) was taken up in sterile water and used as is. Enough of this aqueous solution of [$^{18}F$]fluoride to provide 10–20 mCi of activity (anywhere from 100 to 1000 μl) was added to a borosilicate flask containing 50 μmol of tetraethylammonium bicarbonate as an acetonitrile solution along with 4 additional ml of acetonitrile. The mixture was concentrated under reduced pressure (1 torr) using a nitrogen bleed with the flask in an oil bath set at 65° C. An additional 5 mL of acetonitrile was then added to the mixture which was further concentrated. There was added to the mixture 40 mg (83.3 μmol) of triflate and 4 mL of acetonitrile. The mixture was stirred for 8 minutes under helium at a temperature of 100° C. The reaction mixture was concentrated and 2 mL of 2N HCl was added. The mixture under a nitrogen atmosphere, was heated for 20 minutes in an oil bath set at 125° C. The mixture was than passed through an ion retardation column (BioRad Econo-Pac Ion Retardation column prefilled with AG 11-A8) to effect neutralization, a C18 reverse phase sep-pak (Waters) to effect decolorization and a neutral alumina sep-pak (Waters) to remove fluoride. The [$^{18}F$]2FDG was quantitated using thin layer chromatography on a silica support and, independently on a C18 reverse phase support coupled with BioScan analysis of the TLC plates and measurement of the total radioactivity in the sample with a Capintec monitor. The above procedure was repeated except that in place of the tetraethylammonium bicarbonate phasetransfer reagent, there was used tetraethylammonium hydroxide and tetrabutylammonium bicarbonate. In addition a comparative run was also made with Kryptofix 222-$K_2CO_3$ as the phase-transfer reagent, in accordance with the teaching of K. Hamacher et al, Journal Nuclear Medicine 27:235–238 (1986) except that the intermediate clean-up procedure to remove Kryptofix 222 was replaced with a sulfonic acid functionalized polystyrene resin (Dowex 50X, H= form, 50–100 mesh) at the end of the synthesis. The following results were obtained:

| Reagent | Yields of [$^{18}F$]2FDG | | | |
|---|---|---|---|---|
| | PTR (μmol) | EOB Yield | [$^{18}F$]2FDG Std Dev | n |
| TEAOH | 68 | 4% | | 1 |
| TEAHCO$_3$ | 51 | 48% | 9% | 3 |
| TBAHCO$_3$ | 43 | 63% | 9% | 3 |
| Kryptofix 222-K$_2$CO$_3$ | 67 | 57% | 14% | 4 | where n is the number of runs

The above results show that tetraalkyl bicarbonates of the present invention (TEAHCO$_3$ and TBAHCO$_3$) provide significantly better yields than the corresponding tetraethylammonium hydroxide when employed as a phase-transfer reagent in the synthesis of [$^{18}F$]2FDG. It was further found that when the tetraalkylammonium bicarbonates were used as phase-transfer reagents, in the synthesis of $^{19}F$]2FDG, that tetraethylammonium bicarbonate provided a yield of 41%, tetrabutylammonium bicarbonate provided a yield of 63% and tetrahexylammonium bicarbonate provided a yield of 59%. It was also found that when tetraethylammonium hydroxide was used in combination with potassium bicarbonate at substantially equal molar amounts as the phase-transfer catalyst, a yield of 34% was obtained. However, when tetraethylammonium carbonate was used as a phase-transfer reagent following the same procedure, a yield of only 20% of the [$^{19}F$]2FDG was obtained. In addition, tetraethylammonium hydroxide provided a yield of only 5% while Kryptofix 222-$K_2CO_3$ provided a yield of 44% of the [$^{19}F$]2FDG. These results further confirm the unexpected advantages achieved by employing tetraalkyl bicarbonate phase-transfer reagents in accordance with the present invention.

Although the above example is directed to only a few of the very many variables which can be employed in the practice of the present invention, it should be understood that additional conditions and reagents can be used in the practice of the present invention as set forth in the description preceding this example.

What is claimed is:

1. A method for making [$^{18}$F]fluoro-2-deoxy-D-glucose which comprises,
    (1) contacting at a temperature of 40° C. to 100° C., 1,3,4,6-tetra-O-acetyl-2-0-trifluoromethanesulfonyl-2-deoxy-β-D-mannopyranose and [$^{18}$F]fluoride ion in the presence of a 60 to 95 volume % organic solvent solution of a phase-transfer reagent selected from the class consisting of a tetraalkylammonium bicarbonate, a tetraalkylammonium carbonate and a mixture of a tetraalkylammonium hydroxide and potassium bicarbonate, and
    (2) effecting the substantial removal of the organic solvent, and
    (3) heating the resulting mixture of (2) in the presence of an aqueous hydrogen halide until deprotection of the resulting acetylated 2-[$^{18}$F]fluoro-2-deoxy-D-glucose is effected,
    where the organic solvent of (2) is a member selected from the class consisting of acetonitrile and propionitrile.

2. A method in accordance with claim 1, where the phase-transfer reagent is tetraethylammonium bicarbonate.

3. A method in accordance with claim 1, where the phase-transfer reagent is tetrabutylammonium bicarbonate.

4. A method in accordance with claim 1, where the phase-transfer reagent is tetrahexylammonium bicarbonate.

5. A method in accordance with claim 1, where the phase-transfer reagent is a mixture of tetraalkylammonium hydroxide and potassium bicarbonate.

6. A method in accordance with claim 1, where the organic solvent is acetonitrile.

* * * * *